US008540939B2

(12) United States Patent
Niesz et al.

(10) Patent No.: US 8,540,939 B2
(45) Date of Patent: Sep. 24, 2013

(54) INSTRUMENT AND PROCESS FOR NANOPARTICLES PRODUCTION IN CONTINUOUS FLOW MODE

(75) Inventors: Krisztián Niesz, Báta (HU); Atilla Wootsch, Csömör (HU); Maxime Groualle, Budapest (HU); Zsolt Ötvös, Csongrád (HU); Ferenc Darvas, Budapest (HU)

(73) Assignee: Darholding Vagyonkezelo Korlatolt Felelossegu Tarsasag, Budapest (HU)

( * ) Notice: Subject to any disclaimer, the term of this patent is extended or adjusted under 35 U.S.C. 154(b) by 65 days.

(21) Appl. No.: 12/990,195

(22) PCT Filed: Apr. 28, 2009

(86) PCT No.: PCT/HU2009/000040
§ 371 (c)(1),
(2), (4) Date: Jan. 13, 2011

(87) PCT Pub. No.: WO2009/133418
PCT Pub. Date: Nov. 5, 2009

(65) Prior Publication Data
US 2011/0104043 A1 May 5, 2011

(30) Foreign Application Priority Data
Apr. 28, 2008 (HU) .................................. 0800281

(51) Int. Cl.
*G05B 1/00* (2006.01)
*B01J 10/00* (2006.01)
(52) U.S. Cl.
USPC ........... 422/105; 422/112; 422/630; 422/649; 977/840; 977/901
(58) Field of Classification Search
USPC ................. 422/105, 112, 630, 649; 977/840, 977/901
See application file for complete search history.

(56) References Cited

U.S. PATENT DOCUMENTS

| 5,145,684 | A | 9/1992 | Liversidge et al. |
| 5,858,410 | A | 1/1999 | Muller et al. |
| 6,179,912 | B1 | 1/2001 | Barbera-Guillem |
| 6,607,784 | B2 | 8/2003 | Kipp et al. |

(Continued)

FOREIGN PATENT DOCUMENTS

| GB | 2200048 A | 7/1988 |
| GB | 2269536 A | 2/1994 |

(Continued)

OTHER PUBLICATIONS

International Search Report corresponding with International Application No. PCT/HU2009/000040 dated Sep. 21, 2009, 3 pages (in English).

(Continued)

*Primary Examiner* — Walter D Griffin
*Assistant Examiner* — Lessanework Seifu
(74) *Attorney, Agent, or Firm* — Fitch, Even, Tabin & Flannery LP

(57) ABSTRACT

A continuous flow system for the synthesis of nanoparticles includes a feeding unit connected to the first reactor a flow path, at least one first reactor unit possessing a heatable reactor-zone, a second reactor unit which follows the first reactor in the same cascade; a mixing unit and a second feeding unit between the reactor units, and feeding pumps connected to a raw material source and/or a control unit which is capable of controlling at least one pressure controller and/or controlling the temperature of at least one heatable reactor-zone; each heatable reactor-zone is followed by a cooling unit in the cascade. In addition, a process for the synthesis of nanoparticles, preferably metal-containing nanoparticles, and nanoparticles of biologically active organic molecules wherein the process is accomplished using the system.

14 Claims, 11 Drawing Sheets

(56) References Cited

U.S. PATENT DOCUMENTS

Figure 1:
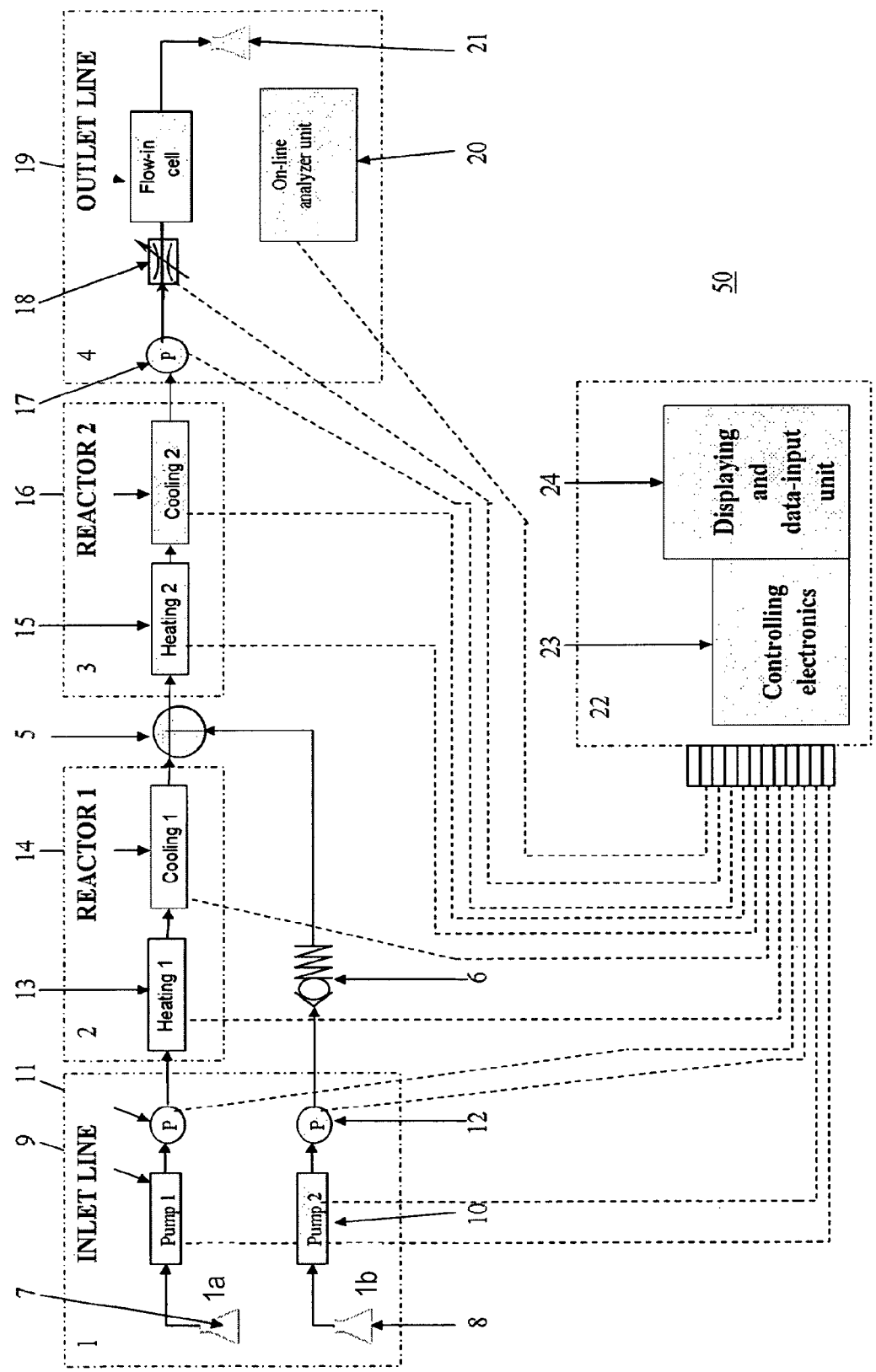

| | | | |
|---|---|---|---|
| 6,682,596 B2 * | 1/2004 | Zehnder et al. | 117/68 |
| 6,884,436 B2 | 4/2005 | Kipp et al. | |
| 2005/0179175 A1 | 8/2005 | Johnson, Jr. | |

FOREIGN PATENT DOCUMENTS

| | | |
|---|---|---|
| WO | WO 92/18105 A1 | 10/1992 |
| WO | WO 01/03670 A1 | 1/2001 |

OTHER PUBLICATIONS

PCT International Preliminary Report on Patentability in PCT/HU2009/000040, dated Jul. 26, 2010, 6 pages.

K. Niesz et al., "Nanoparticle synthesis completed with in situ catalyst preparation performed on a high-pressure high-temperature continuous flow reactor" Microfluidics and Nanofluidics, Springer, Berlin, Germany, vol. 5, No. 3, Jan. 25, 2003, pp. 411-416.

* cited by examiner

Table 1

| Applied cooling | Mean particle size (nm) | | | | |
| --- | --- | --- | --- | --- | --- |
| | 1. experiment | 2. experiment | 3. experiment | 4. experiment | 5. experiment |
| Air-cooling | 9.3 | 11.8 | 10.4 | 8.2 | 14.8 |
| Countercurrent heat-exchanger | 3.6 | 3.6 | 3.7 | 3.9 | 3.8 |

FIG. 10

INSTRUMENT AND PROCESS FOR NANOPARTICLES PRODUCTION IN CONTINUOUS FLOW MODE

CROSS-REFERENCE TO RELATED APPLICATIONS

This application is the U.S. National Phase of International Application PCT/HU2009/000040, filed Apr. 28, 2009, claims priority benefit under 35 U.S.C. §119 to Hungarian Patent Application No. P0800281, filed Apr. 28, 2008, both of which are incorporated by reference herein in their entirety.

The subject of this application is a device for the preparation of nanoparticles in continuous flow system which consists of a first feeding unit connected to the flow path and at least one reactor unit possessing a heatable reactor zone in the same cascade.

It is known that the nanoparticles are entities having the size of nanometer magnitude and they form a border-line between the atoms, molecules and the macroscopic matter that is formed from them. By decreasing the particle size of the macroscopic materials, their properties can change considerably when approaching the nanometer magnitude, since in this region the number of atoms on the surface is not negligible compared to the total.

The properties of matter in the nanometer-range are of great interest both in the scientific and the industrial point of view. However, while the physical properties of the macroscopic matter does not depend on its size, the properties of nanoparticles are remarkably size-dependent in most cases. For this very reason, there is a serious demand for the development of such a device and process that are capable of the fast and reliable synthesis of nanoparticles of different type and structure and having narrow particle size distribution. Here 'different structure' can mean nanoparticles that are composed of one component (monostructured nanoparticles), two or more component (composite nanoparticles). A subgroup of composite nanoparticles is 'core-shell'-type nanoparticles in which one or more components form the core of the nanoparticle and also one or more components form a shell (coating) around the core.

Today both batch-type and continuous-type reactors are used for the synthesis of nanoparticles. The batch-type reactors are more economic when the batch size is bigger. The bigger batch size, on the other hand, results in a less uniform particle size distribution.

A simple reactor for the synthesis of in situ catalysts is described in Microfluid Nanofluid 2008, 5, 411-416. Continuous flow tubular microreactor system is described in Nanoletters 2004, 4(11), 2227. This system is used only for the production of silver nanoparticles. Silver nanoparticles are synthesized by the device disclosed in U.S. Pat. Appl. 2005/0179175. The particles are formed from vapors of the precursor.

It is also known from the literature that both the pharmaceutical discovery and industry face with the problem of low water-solubility of APIs and biologically active molecules. The classical drug formulation techniques employ micronisation methods to increase solubility. The size of the particles produced by these methods is between 2 and 5 µm. In several cases, micronisation does not effectively increase the solubility and does not solve the problem of low bioavailability. Decreasing the particle size further towards nanometer range can offer a solution for this problem.

Technologies which are capable of producing drug nanoparticles can be classified into two groups: bottom-up (precipitation of nanosize particles from solution) and top-down (decreasing the size of micronised particles towards nanometer magnitude). The size of nanoparticles is typically under 1 µm.

The two top-down technologies which are extensively employed in pharmaceutical industry are high-pressure homogenization (see Dissocubes®: U.S. Pat. No. 5,858,410 or Nanopure: PCT/EP00/06535, also Nanoedge™: U.S. Pat. No. 6,884,436) and milling (see Nanocrystal™: U.S. Pat. No. 5,145,684). These techniques have the following disadvantages. None of them is capable of continuous production of nanoparticles; the material needs pre-treatment (micronisation); optimization of reaction parameters is difficult and time-consuming. They require large amount of material, thus, they cannot be used (or only with high costs) in the drug development stage. Milling requires large amount of energy, thus, these systems have to be cooled as well. The crystal structure can be changed during milling because of the heat-effect. The handling of nanodust (particles under 250 nm) is dangerous and requires special safety regulations.

Bottom-up technologies (see e.g. Hydrosol: GB 2,269,536 and 2,200,048 or U.S. Pat. No. 6,607,784) are not used in pharmaceutical industry for the production of nanoparticles, since stable control for obtaining uniform particle size is difficult. Control of precipitation is difficult and optimization of reaction parameters is laborious and time-consuming. Some continuous systems are also known which are capable of producing microgram quantities of metal-containing nanoparticles through chemical reaction. These reactors, however, can usually be used for the production of nanoparticles containing only one metal. Additionally, the circle of applicable solvents are narrowed by the fact that the known continuous reactors work at atmospheric pressure, thus, the boiling point of the solvent delimits its use in case of nanoparticles that requires certain temperature for their synthesis.

U.S. Pat. No. 6,179,912 describes a microfluidic continuous flow reactor system for the production of fluorescent nanoparticles. The system contains two reactors in a cascade. The reactors can be heated to different temperatures, but it is not possible to feed the solution of a new reagent between the two reactors. The mixing of the reagents is accomplished before they enter to the first heatable reactor unit, thus, this reactor system can only be used for the synthesis of such multicomponent nanoparticles where the distribution of the components inside the nanoparticles is homogeneous or random. Therefore this system is not capable for the production of core-shell nanoparticles. The size of the produced nanoparticles is controlled by the length of the heated reactor unit, however, changing this parameter during the reaction is laborious, thus, the reactor-system can be optimized typically for the synthesis of one type of nanoparticle. Additional disadvantage is the limitation of boiling point of the solvent, since the system works at atmospheric pressure. Thus, only those solvents can be used which are liquids at the temperature of the reaction i.e. typically high boiling organic solvents.

The aim of this invention is to get over the failures and shortcomings of the devices of the present state of technology, especially to provide such continuous flow device and process for the synthesis of nanoparticles in which the properties of the produced nanoparticles can be modified during the process by changing/optimizing the working parameters of the device together with the process parameters in order to obtain nanoparticles having the desired structure and properties.

The set targets of the invention, i.e. changing the particle size of the synthesized nanoparticles during the synthesis of nanoparticles are reached secondarily by such continuous flow device The above target, i.e. the modification of the properties of the synthesized nanoparticles during their synthesis, is achieved on the one hand by constructing a device for the preparation of nanoparticles in continuous flow system which consist of a first feeding unit connected to the flow path and at least one reactor unit possessing a heatable reactor zone in the same cascade.

Thus, the invention is the 50 continuous flow system for the synthesis of nanoparticles which consist of the 1a feeding unit connected to the flow path, at least one 2 first reactor unit possessing the 13 heatable reactor-zone, the 3 second reactor unit which follows 2 in the same cascade; the 5 mixing unit and the 1b second feeding unit between 2 and 3 reactor units, the 9 and 10 feeding pumps connected to the raw material source and/or 22 control unit which is capable of controlling at least one 18 pressure controller and/or controlling the temperature of at least one 13 heatable reactor-zone; each 13 heatable reactor-zone is followed by 14 cooling unit in the cascade.

The device of invention contains 14 cooling unit which follows 13 heatable reactor-zone in the cascade as parts of 2 reactor unit.

A beneficial embodiment of the invention contains a unit for analysis (4) of the final product which follows the last reactor unit (3) in the flow path and has a DLS-analyzer (Dynamic Light Scattering).

In addition, the subject of this invention is the application of the device described above for the synthesis of nanoparticles from one, two or more constituents, preferably metals; nanoparticles, nanoemulsions, nanosuspensions and colloidal solutions containing biologically active organic molecules, and core-shell-type nanoparticles.

A beneficial embodiment of the invention is suitable for the synthesis of API-nanoparticles.

The invention also covers the process for the preparation of nanoparticles preferably containing metals or biologically active organic molecules when they are synthesized by the device described above.

A preferable embodiment of the invention uses non-steroidal anti-inflammatory molecules, drugs used against erectile dysfunction/pulmonary hypertension, sartan-type compounds, statin-type compounds, anti-cholesterol compounds and the synthesis is carried out in continuous flow system.

The synthesized nanoparticles are analyzed in order to determine the levels of the desired properties and the process parameters can be changed if needed. Such parameter is the temperature of the heatable reactor-zone. A well-known effect of high temperature is that it increases reaction rates which in turns accelerates synthetic processes. The relatively broad region of applicable temperatures (10-350° C.) enables the synthesis of different types of nanoparticles which makes the reactor a general tool for the synthesis of nanoparticles. Increasing the temperature, however, may result in boiling of some solvents of the starting liquid delivered by the feeding unit to the heated reactor-zone where the solvent evaporates and the dissolved material precipitates out. In the continuous flow systems of the present state of technology, the precipitation is prevented by choosing a solvent which has a boiling point high enough for the planned reactor-temperature. However, this makes impossible to change the temperature of the reactor considerably during the process according to the online analytical results of the produced nanoparticles. If the used temperature of the reactor does not furnish nanoparticles having the desired properties, the synthesis have to be redesigned by choosing another solvent for the starting materials in some cases which increases the time needed for the optimization of the reaction considerably.

The advantage of the device of invention is that the progress of the synthesis can be changed and controlled during synthesis, since the system provides high degree of flexibility regarding the starting liquid containing one or more starting materials. Here 'starting liquid' typically means a starting reagent solution or, as it is going to be discussed in details later, recycled colloidal solution in which the starting materials needed for the synthesis of nanoparticles are present in dissolved or dispersed form. The main part of the starting liquid can be a solvent or a 'delivering liquid' which does not dissolve the starting material of the nanoparticle synthesis. This description mainly uses the word 'solvent' for the sake of simplicity; however, the facts which are stated about the 'solvent' obviously apply to the 'delivering liquid' as well.

In case of the continuous flow systems of the present state of technology, the solvent being the main part of the starting liquid have to be chosen to match with the temperature of the reaction needed for the nanoparticle-synthesis. Thus, in case of the reactors of the present state of technology, low-boiling solvents (delivering liquids) cannot be used. This limitation does not apply to the device of invention, since by increasing the pressure in the reactor-zone, the boiling point of the applied solvent can be increased in order that it should always be higher than the temperature of the reactor-zone i.e. the solvent would never boil. Thus, using high pressure (1-250 bar) broadens the group of applicable solvents remarkably, while the yield of the reaction can also be increased considerably without unwanted precipitation.

According to the invention, low-boiling (volatile) solvents are exemplified but not limited to the following solvents: methanol, ethanol, propanol, isopropanol, ether, dichloromethane, chloroform, toluene, acetone, water and mixtures of any of these.

In addition to the advantages mentioned above, applying high pressure and temperature together, the supercritical state of the applied solvent can be reached. A state, where properties are still to be investigated and might improve reactions' outcome. Thus, the device of invention enables the synthesis of nanoparticles under supercritical conditions, providing a new horizon of nanoparticle research and synthesis.

Using the device of invention, API-nanoparticles of the size of a few nanometers can also be synthesized safely. The material consumption of the continuous flow system is minimal, thus, it can offer a solution for nanoization of biologically active molecules even in the drug development stage. Since there is no heat-evolution during nanoization, the risk of structural rearrangement of the synthesized nanoparticles is minimal. Nanoparticles synthesized by the device of invention are obtained as colloidal solutions or nanoemulsions or nanosuspensions, thus, the strict regulations for handling nanodusts are not applied here.

The device of invention can contain an online DLS-analyzer (Dynamic Light Scattering) which enables the continuous monitoring and checking of the size of the synthesized nanoparticles during synthesis. This option is not available in case of other known devices.

The set target of the invention, i.e. changing the particle size of the synthesized nanoparticles during the synthesis of nanoparticles are reached on the other hand by such continuous flow device, which contain a first feeding unit connected to the flow path and at least one first and one second reactor unit. Essential part of the device is the mixing element present between the two reactor units, and a second feeding unit which is connected to the flow path through this mixing unit. The role of this second feeding unit is to provide a second starting liquid in order to alter a given property of the intermediate product of the first reactor unit.

Using the second feeding unit, it is possible to add another reagent to the nanoparticles synthesized by the first reactor unit. As a result, the properties of the nanoparticles coming from the first reactor unit can be modified in the second reactor unit. For instance, it is possible to create a coating on the surface of the nanoparticle which modifies the properties of the nanoparticle or to synthesize multicomponent and multifunctional materials under controlled conditions.

Similarly, by placing further reactor units after the second reactor unit and connecting further feeding units to the flow path through mixing elements between each two reactor units, the resulting nanostructures can be modified further and further in each additional reactor unit to enable the synthesis of nanoparticles having several different layers of coating on the core which is formed in the first reactor unit.

The parameters can be adjusted in situ in this case as well. By analyzing the nanoparticles leaving the second reactor unit, it is possible to obtain information about the evenness of the coating, the ratio of the core-material and coating; and also possible to change the process parameters (the temperature of the first and second reactor-zones, the flow rate of the first and second starting liquids etc.) during reaction.

In case of a particularly beneficial form of the device and process of the invention, the final product that leaves the last reactor unit is analyzed optically and some particular device- and process parameters of the running reaction can be adjusted according to those analytical results. For instance, using a flow-in cell together with a UV/Vis spectrophotometer or an on-line DLS-analyzer (Dynamic Light Scattering) it is possible to analyze on-line the nanoparticles of the final product qualitatively.

Figure 5:
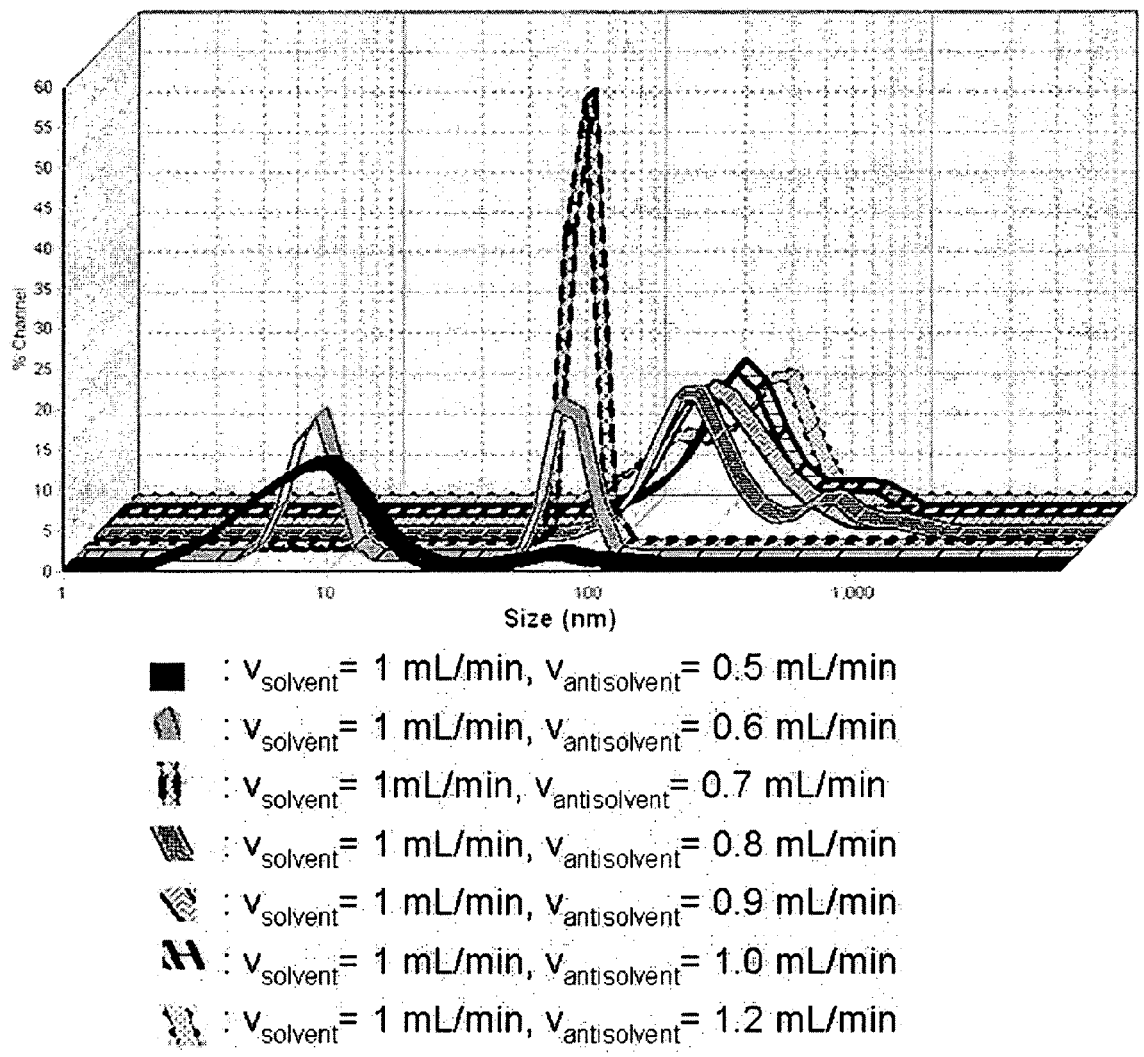
Figure 6:
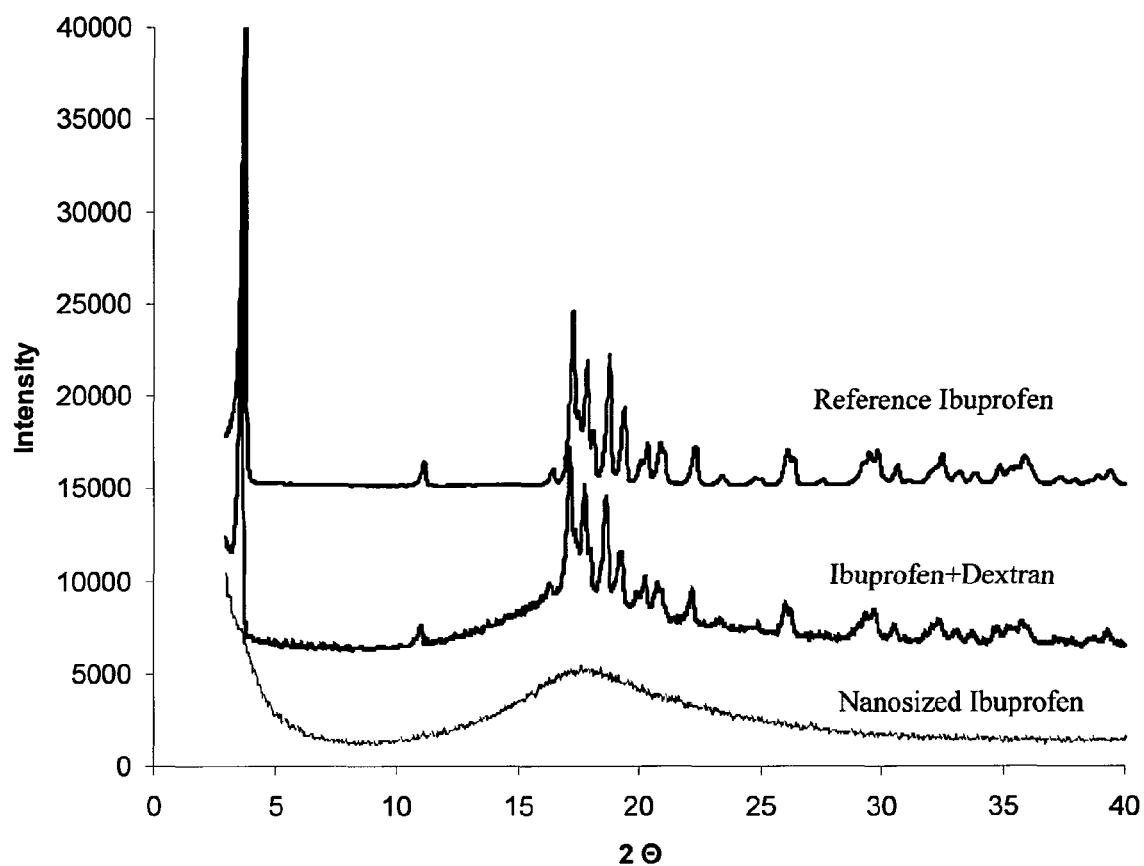
Figure 7:
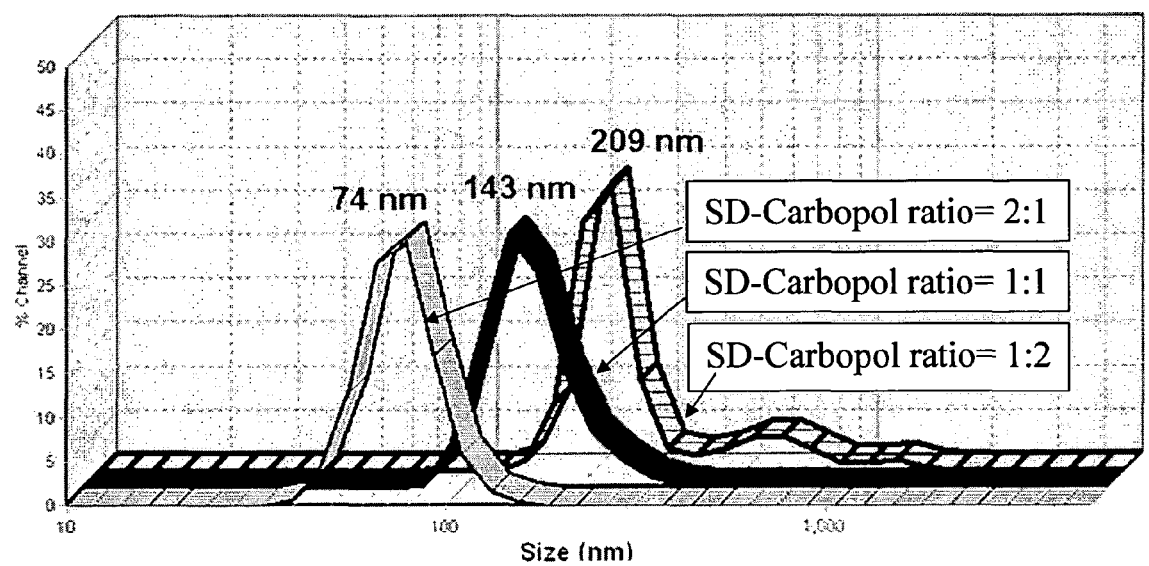
Figure 8:
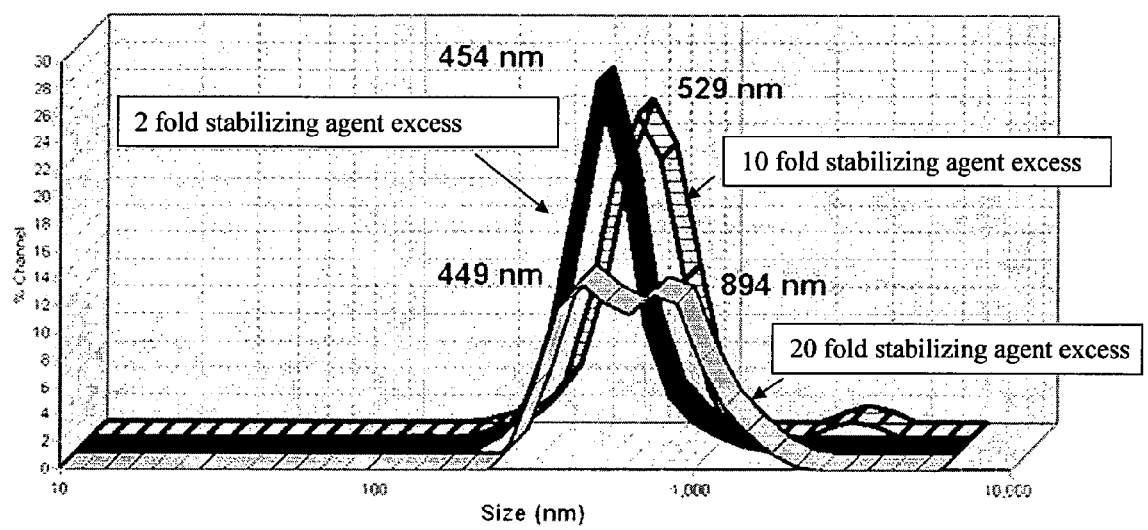
Figure 9:
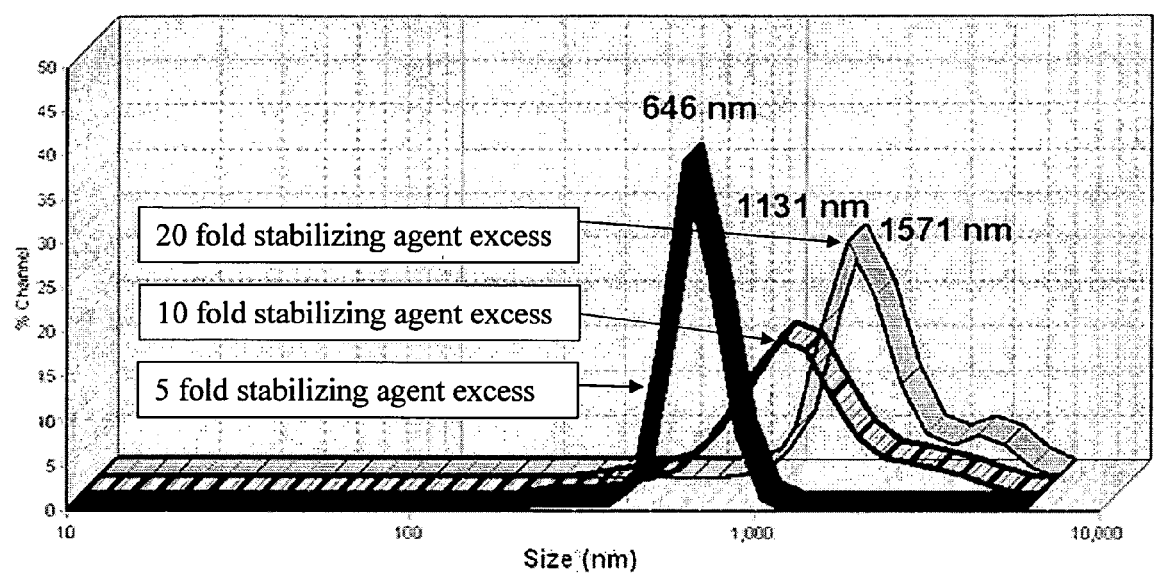

Further details of the invention are demonstrated by particular examples of its accomplishment depicted on the following figures. On FIG. 1, the block-diagram of a beneficial form of the device of invention, FIG. 2a-2c, TEM (Transmission Electron Microscope) images of Pt nanoparticles in case of different flow rates, FIG. 2d, the dependence of mean particle size as a function of the applied flow rate, FIG. 3, TEM image of a Pt—Fe bimetallic nanoparticle, FIG. 4a, TEM image of CdSe nanocrystals, FIG. 4b, emission spectra of colloidal solutions of CdSe nanocrystals synthesized using different flow rates can be seen;

FIG. 5, size and size distribution of the synthesized nanoparticles prepared at different flow rates, FIG. 6, X-ray diffractograms of reference Ibuprofen, nanosized Ibuprofen and the physical mixture of the ingredients, FIG. 7, size and. size distribution of the synthesized nanoparticles prepared at different SD-Carbopol ratios, FIG. 8, size and size distribution of the synthesized nanoparticles using different ratios of active ingredient and stabilizer, FIG. 9, size and size distribution of the synthesized n.anoparticies using different ratios of active ingredient and stabilizer, and FIG. 10, mean particle sizes of prepared platinum nanoparticles using different types of cooling.

FIG. 1 shows the block-diagram of a beneficial form of the 50 device of invention. The device 50 is a continuous flow laboratory device for the synthesis of nanoparticles applicable in wide range of pressure (1-250 bar) and temperature (10-350° C.) which consist of a first feeding unit (1a) and a second feeding unit (1b); a first reactor unit (2) and a second reactor unit (3) connected to the same cascade as 1a, followed by the product collecting and analyzing unit (4); the mixing unit (5) which is connected to 1b via check-valve (6) and placed between reactor units 2 and 3; and the control unit (22).

Feeding units 1a and 1b contain the starting material source of nanoparticle synthesis, in the present case these units are starting material reservoirs 7 and 8. The starting liquid which contains the starting material or materials can be introduced through a line attached to feeding unit 1a or 1b; in this case this line serves as the source of the starting material(s). Feeding units 1a and 1b also contain feeding pumps 9 and 10, and manometer 11 and 12, respectively. Typically, starting liquids are solutions or colloidal solutions; thus, any suitable liquid pump can serve as feeding pumps 9 and 10. Required flow rates, typically between 0.1-10 ml/min, can be set by feeding pumps 9 and 10. For example, Knauer® double isocratic HPLC pumps, characterized by 400 bar maximal operating pressure at a flow range of 0.01-10 ml/min, can serve as feeding pumps 9 and 10. Their error is less than 2% at 5 ml/min. Such pumps are extensively used for washing HPLC columns, to inject liquid samples of larger volumes and to carry eluents against pressure.

Reactor units 2 and 3 contain heatable reactor zones 13 and 15, followed by cooler devices 14 and 16 in the flow path. Reactor zones 13 and 15 are preferably heat- and pressure-resistant coil-pipes working in continuous flow, in which the temperature of the reaction mixture is controlled by a heat-conducting medium up to 350° C. Application of electrically heated coil-pipe-type heat-conducting heating-elements, e.g. VICI® type Hastelloy C coil-pipe type heating-elements is advantageous. In this case the outer diameter is ¹⁄₁₆", while the inner diameter is 0.03". The length of the temperature-controlled part of the reactor zone 13 and 15 is 3200 mm, the heating power is 144 W and the consumption is 12 A. Temperature can be adjusted and controlled up to 350° C.±1° C.

Cooling units 14 and 16 are countercurrent heat-exchangers, in which the hot media coming out from heating units 13 and 15 encounters the room-temperature media of the heat-exchanger in contraflow. Heat-exchangers contain tubes that are brazed to each other. These tubes can be e.g. Hastelloy C type tubes manufactured by VICI®. The outer diameter of the tube is ¹⁄₁₆", the inner diameter is 0.03". The useful length of the heat-exchangers is 1200 mm.

Mixing unit 5 placed between the first and second reactor units 2 and 3 can be any suitable passive or active mixing unit. One of the most simple passive mixing elements is a confluent T element, through which the second starting liquid from feeding unit 1b flows into the product solution coming from reactor unit 2. To operate as mixing unit 5 e.g. VICI® type stainless steel T element is convenient. Such mixing unit 5 has e.g. 1 mm bore and a tube with ¹⁄₁₆" of outer diameter can be attached to it.

The flow of the substance from the direction of mixing unit 5 to the second feeding unit 1b is preferably prevented by check valve 6 (e.g. the stainless steel product of ThalesNano Inc., Budapest), working in a pressure range from atmospheric pressure up to 250 bar. Preferably, check valve 6 resists aggressive chemicals, thus, can be used in a case of any kind of starting liquids.

Unit 4, which is for collecting and analyzing reaction products, in this configuration contains manometer 17, pressure controller 18, flow-in cell 19, on-line analyzer unit, in particular an optical detector 20, and product reservoir 21.

In device 50, pressure is controlled by data deriving from manometers 11, 12 and 17 and by pressure controller 18 controlled by control unit 22. Manometers 11, 12 and 17 can be e.g. Knauer® type devices originally designed for HPLC (High Pressure Liquid Chromatography) purpose, with an operating pressure up to 400 bar.

Pressure controller 18 is e.g. a pressure control valve (developed by ThalesNano Inc., Budapest, Hungary), suitable for the accurate control of high pressures in case of instruments working at high flow rates by volume, such as used in case of high-pressure liquid chromatography applications.

In preferably cases, device 50 can be integrated with an on-line detector 20, that can be e.g. such spectroscopic unit, which was used in Example 3 (described below) for the continuous flow analysis of semiconductor type CdSe nanocrystals. In this case, a USBLS450 type LED, emitting at 465 nm, was used as the light source. The detector can be e.g. an USB2000-type small-sized device equipped with a CCD detector operating between 200 and 1100 nm, or a Dynamic Light Scattering instrument (Nanotrac, a light scattering instrument equipped with a 3 mW diode laser operating at 780 nm; measurement range: 0.8-6500 nm) which is suitable for the on-line determination of particle size and particle size distribution in case of various nanoparticles (see Examples 6 and 7).

Preferably, control unit 22 is connected with each device controlling or measuring any operating parameter and controls them. These devices are feeding pump 9, manometers 11, 12 and 17, pressure controller 18, heating devices of reactor-zones 13 and 15, and cooling units of reactor units 2 and 3. Control unit 22 preferably consists of the controlling electronics 23 and the data-input and displaying unit 24, by which the operator can manually set the required operating parameters of device 50 as well, such as flow rates of the first and second feeding pumps 9 and 10, the pressure and temperature in the reactor-zones 13 and 15 of the first reactor unit 2 and the second reactor unit 3, respectively.

It is noted that in case of the device represented in FIG. 1, pressure is controlled in one point, by pressure controller 18, thus, the pressure is the same along the whole cascade. However, extra 18 pressure controllers can be inserted at other points, by which different pressure values for reactor zones 13 and 15 can be set.

The process of the invention is implemented by device 50 according to FIG. 1, the operation of which is the following:

Solutions containing starting compounds and coming from feeding unit 1a get into reactor unit 2 at the corresponding pressure and flow through the reactor-zone 13 heated up to the corresponding temperature, with a flow rate controlled by feeding pump 9. Time spent in reactor-zone 13 is determined by the flow rate, therefore feeding pump 9 controls the reaction time in reactor-zone 13. Reaction time is set as to enable the required reaction to complete and the first intermediate product to be formed. In the cooling unit 14 of reactor unit 2, the first intermediate product is cooled down to the required temperature, then it is combined and mixed in the mixing unit 5 with the second starting liquids (compounds) coming from feeding unit 1b, and they together attain reactor unit 3, where, in a similar way as described above, further reactions take place in the same controlled way. Reactions taking place in reactor units 2 and 3 include particle formation and growing. In this configuration, the 50 device of invention is a duplex reactor-system, in which the synthesis of the nanoparticles occurs. The final products are analyzed by the on-line detector 20 in the flow-in cell 19, and collected in the product reservoir 21.

Control unit 22 controls feeding pumps 9, 10 and pressure controller 18 by the parameters set by the operator and/or by the data measured or collected by the devices connected with control unit 22; as well as it controls the temperature of reactor-zones 13, and cooling units 14, 16, thus providing the required flow rates, pressure and temperature values.

The temperature of reactor-zones 13 and 15 can preferably be regulated from 10° C. even up to 350° C. By the help of feeding pumps 9 and 10, manometers 11, 12 and 17, and the controllable pressure controller 18, the 50 device of invention is also applicable to perform reactions even at 350 bar pressure. Liquid pumps 9 and 10 are capable to provide a flow rate of even 10 ml/min in the whole system.

At the end of the synthesis the whole amount of the used solvent and chemicals can be collected, discarded if necessary, or utilized e.g. can be used in a reaction again if it is needed, in another device or in the device of invention 50 (i.e. can be recycled); this way the procedure is environmental-friendly.

The duplex reactor-system of device 50 enables the accomplishment of various reactions in the reactor-zones 13 and 15 which are well-separated reaction chambers. To both reactor-zones (13 and 15) cooling units (14 and 16, respectively) are attached directly enabling that reaction products can immediately be cooled after leaving reactor-zones 13 and 15 and, through this, the immediate cease of the (synthesis) reaction. This way the temperature and the reaction can well be controlled, and the device become suitable for producing nanoparticles in the form of mono-dispersive systems, i.e. the size of the synthesized particles will be in a narrow range which is e.g. 1-3 nm in the case of metal particles. However, this range can be controlled precisely by the accurate set-up of reaction parameters. In particular cases, the unit for collection and analysis of reaction products (4), connected to the second reactor unit 3, includes an on-line analysis unit, e.g. optical detector 20, which analyzes the amount and the quality of the final products within a short time (30 sec).

If there is a need to use reaction products (typically the colloidal solution of nanoparticles), emerging from reactor unit 2, as the starting liquid of further reactions in the second reactor unit 3 and addition of a further reagent or its solution is necessary, this new reagent (solution) can be introduced into the system via mixing unit 5. The flow of the solutions into reactor 15 is controlled by check valve 6.

By the data-input and displaying unit 24 of control unit 22, flow rate, temperature and pressure values of the required reaction can be set. The controlling electronics 23 is connected on the one hand to the data-input and displaying unit 24, and, on the other hand, to the feeding pumps 9 and 10, the heating units of reactor-zones 13 and 15, cooling units 14 and 16, manometers 11, 12 and 17, pressure controller 18 and optionally to the on-line detector 20. Its function is to provide the flow rates, temperatures and pressure values that had been set previously and, optionally, to display the results measured by the on-line detector 20 in an appropriate form. Based on the results of the on-line analysis of a property, e.g. particle size, of the produced nanoparticle, control unit 22 can automatically modify the operating parameters of device 50, or an operator can change one or more parameter values to obtain the required properties. In case of properties depending on particle size, the changed parameter is typically the flow rate or the temperature. In both cases proper setting of the pressure can also be necessary at the same time. For example, in a particular case, together with increasing the temperature of the reactor-zones 13, 15 the boiling point of the solvents used for the starting liquids is reached, and in this case control unit 22 can automatically increase the pressure according to the boiling point-pressure diagram of the solvent (given in advance), keeping the boiling point of the solvent higher than the temperature of the reactor-zones 13 and 15.

Preferably, the controlling electronics 23 consists of one or more microcontroller units or one or more computers suitable for real-time control, or the combination of the two.

The data-input and displaying unit 24 can be a device with any working principle appropriate for displaying several characters or graphical information (LED, LCD, etc., displays or CRT, LCD and other types of displays). The data input unit can equally be a specially designed device consisting of separate buttons, conventional keyboard or touch screen.

Implementing the process of the invention it is possible to synthesize nanoparticles of noble metals, preferably, gold (Au), platinum (Pt), palladium (Pd), ruthenium (Ru), rhodium (Rh), iridium (Ir); semiconductor type (CdSe) and magnetic (Co, $Fe_2O_3$) nanoparticles. Using the device according to FIG. 1, complex nanoparticles can be obtained by the application of two starting solutions e.g. the alloys or the bimetals of the above metals, or the "core-shell-type" nanoparticles, or the combination of the above elements (metal-semiconductor, magnetic-semiconductor, metal-magnetic).

The particle size range of the obtained final products is 1-10 nm and can be changed selectively. The fields of application of the produced nanoparticles can be as follows: solar cells, assembling of microelectronical circuits, laser technique, LED-construction, and biomedical applications such as diagnostics in cancer research.

Application of device 50 in FIG. 1 for the synthesis of different types of nanoparticles is demonstrated thereafter, without restricting the application of the device of the invention to those mentioned below.

The applied technique: the synthesis of metals in liquid phase by their reduction with alcohols at high temperatures, and obtaining metals from metal ions by reduction, e.g. with hydrogen, hydrazine, borohydride or alcohols according to reactions described in the literature.

Preparation of the starting solution: a metal-containing reagent (for example any platinum salt) is dissolved in any alcohol, preferably in ethanol or methanol in the presence of a stabilizing agent (any polymer, preferably poly(vinyl-pyrrolidone). Stabilizing agent is applied to prevent the aggregation of the nanoparticles formed in the reaction.

Device 50 is used to produce single-metal nanoparticles as a first application according to the followings.

The staring liquid (solution of the reagent) is placed in the starting liquid reservoir 7, from where feeding pump 9 pumps it into first reactor unit 2. In case of the synthesis of single-metal nanoparticles, only feeding unit 1a (i.e. a unit consisting of starting liquid reservoir 7, feeding pump 9 and manometer 11) and only one reactor unit, e.g. reactor unit 3 is necessary. Using feeding pump 9, the starting liquid is pumped through the reactor unit 2, no reactions take place in this reactor; reactor-zone 13 is not heated, it is at room temperature. Then the mixture gets into the second reactor unit 3 through mixing unit 5 (T element), the line of which leading to the second feeding unit 10 is closed by check valve 6. In the second reactor unit 3 reactor-zone 15 is heated to the temperature according to the actual reaction, therefore, reduction take place here: alcohol reduces metal ions to metal. The polymer based stabilizer which is stable at this temperature (no decomposition) prevents the metal nanoparticles from the aggregation due to its steric stabilization effect. Cooling unit 16 following reaction-zone 15 in the cascade cools the solution rapidly to room temperature, this way impeding the further, undesirable continuation of the reaction. In this way, the size of the nanoparticles can easily be controlled by the proper setting of the flow rate and the temperature. The reaction product is a colored colloidal solution, the color of which depends on the nature of the metal and the particle size of the product, e.g. brown (noble metals) or e.g. greenish red (in case of CdSe). During the synthesis of semiconductor nanoparticles, optical analyzer can be applied as on-line analyzer unit, preferably spectrophotometer or dynamic light scattering instrument (detector 20), since in this case the optical features of the obtained colloidal solution largely depend on the size of the nanoparticles in it. The semiconductor nanoparticles (e.g. CdSe) absorb and emit light at different wavelengths depending on their particle size. During the synthesis of nanosized metal particles, however, optical analyzer has no such use, as in this case this effect is not as considerable. Optical detector 20 can be used as well during the synthesis of gold- and silver nanoparticles, however, in these cases absorption depends on surface plasmones (the collective movement of the electron shell).

Device 50 is used to synthesize bimetallic or core-shell-type nanoparticles as a second application, as follows.

In this case, both the first (1a) and the second feeding unit (1b) are used. The base-nanoparticle is generated in the first heated reactor unit 2, e.g. a platinum nanoparticle is generated from the starting liquid stored in vessel 7. To this end, the solution of the second starting material stored in the second starting liquid reservoir 8 is pumped by feeding pump 10 into reactor-zone 15 through mixing unit 5. If the aim is to increase the size or to change the shape of the Pt-nanoparticles, the second starting liquid can be again platinum-containing solution. Otherwise another metal-containing solution, e.g. iron-solution. In the latter case, the reaction product is a bimetallic system. Core-shell-type semiconductors are produced by the same way: the core of the semiconductor is produced in reactor unit 2, while in the second reactor unit 3, the 'shell' covers the particles, such as in the case of cadmium selenid/zinc sulphide (CdSe/ZnS) semiconductor quantum dots. In this procedure, the solution of the starting material required for the production of the ZnS shell is fed by the second feeding pump 10, through mixing unit 5, which is situated between the first and second reactor units 2 and 3. This starting material decomposes at the high temperature of the reactor-zone 15 of the second reactor unit 3 and covers the earlier-formed CdSe core as a coating. CdSe/ZnS-type composites have extraordinary importance in case of the production of solar cells, since they have large quantum efficiencies and they are exceptionally stable and resistant materials.

In the application using both reactor units 2 and 3, device 50 of this invention is also appropriate to produce metal-containing nanoparticles according to combinatorial chemistry principles. This includes for example mixing of semiconductors with metals, e.g. Cd/Se/Au, or with magnetic nanoparticles, Cd/Se/Fe, Cd/Se/Co, or Cd/Se/$Fe_2O_3$.

The second metal can be built in randomly into the first, they can form alloy or structured system (core-shell bimetallic systems), it can diffuse into the first metal or it can even form a layer around the first one. All these depend on the applied metals, starting materials, solvents or delivering liquids and the conditions (temperature, pressure, flow rate) applied for the two-step reactions. Using the device 50 of this invention, practically any combination of the above parameters can be accomplished, for this reason combinatorial chemistry principle was referred. This way, by the application of hundreds or even thousands of parameter combinations, the nanoparticle can be found that meets the expectations the best.

Three-, four- or multi-metal systems are also applied in the industry (e.g. in the car-industry Pt, Pd and Rh noble metals are used in the three-line catalytic converters). Such nanoparticles can also be produced by device 50. This is done by carrying out consecutive reaction steps in which the end-products collected in the final product reservoir 21 are used as the starting materials in the following reaction. Another possibility is to extend device 50 by a third feeding unit and reactor unit, as well as by a second mixing unit and check valve in order to be possible to add the third starting liquid from the third feeding unit to the intermediate product leaving the second reactor unit 3.

The fact, that homogeneously distributed metal nanoparticles cannot be obtained by the preparation of starting solutions of two or several metals and by feeding them into only one reactor, emphasizes the advantages of device 50 including two or more reactor units 2 and 3. Reaching the desired result in a controllable system can be assured by consecutive reactions.

As it had been written above, the nanoparticles produced in the device of this invention are used directly. Necessarily, the produced nanoparticles can also be obtained in solid form from its colloidal solution by the known methods of the present state of technology. This, for example, can simply be carried out by mixing the colloidal solution with an organic solvent (for example with hexane, preferably), then by the separation or centrifugation of the precipitated particles. However, if the nanoparticles are needed to apply in colloidal solution again, then nanoparticles obtained in solid form can be dispersed again with suitable solvent. This procedure can be applied for the purification of nanoparticles as well.

We note that the application of the countercurrent heat-exchanger of this invention leads to more reproducible results in case of the synthesis of nanoparticles of biologically active compounds, such as API nanoparticles. In our implementing experiments, nanoparticles were prepared from the dimethyl sulphoxide solution of the active pharmaceutical ingredient (API) by the application of water as an anti-solvent and Carbopol 980 as a polyelectrolyte-forming reagent. Without the application of the heat-exchanger a 5-8° C.-increase of the temperature was observed during the mixing of the dimethyl sulphoxide and water (heat of mixing). This increase in temperature leads to undesirable side-reactions; sometimes, the post-polymerization of Carbopol 980 (a polyacrylate derivative weakly cross-linked by allyl pentaerythritol). As the result of the post-polymerization, the weakly cross-linked polymer network caused the formation of micron sized aggregates. By the application of the heat-exchanger, the increase of the temperature observed in the reactor-zone can be diminished, thus, the side-reaction can entirely be eliminated by controlling the temperature.

The operation and the characterization of the features of the device 50 of the invention is demonstrated by the following examples:

EXAMPLE 1

Preparation and Size-Selective Optimization of Platinum (Pt) Nanoparticles

In the first step a starting solution was prepared in the following way: $6 \times 10^{-3}$ M hexachloroplatinic acid $H_2PtCl_6 \times 6H_2O$ (Aldrich) solution was prepared as a mixture of methanol: water=9:1, then PVP polymer (poly(vinyl-pyrrolidone), Aldrich) was added in 10-fold monomer excess to $Pt^{4+}$ ions. The role of the polymer is to prevent the aggregatior of Pt nanoparticles, in order to obtain a stable colloidal solution as the result of the synthesis.21

In the second step reaction parameters (temperature, pressure, and flow rates) were set by the 22 control unit. The experiment was carried out by using 1 mL/min flow rate, 150° C. reaction temperature (in the first 2 reactor unit's 13 reactor zone) and 45 bar pressure.

Before the reaction, the experimental system was flushed with methanol which was pumped into the 2 reactor unit by the 9 feeding pump. After confirming that the system does not contain any impurities and the 13 reactor zone keeps the set parameters constantly, the starting solution was placed into the 7 starting liquid reservoir and the feeding pump was started. Using the mentioned 1 mL/min flow rate, it took 5 minutes until the first drops of the synthesized colloidal solution appeared in the 21 product reservoir. Due to the continuous and systematic changing of the reaction parameters, fast and size-selective optimization of the Pt nanoparticle synthesis could be achieved. During the synthesis, flow rate was varied between 0.2 and 3 mL/min, the produced colloidal solutions were collected in separate vials. Analysis of the samples was carried out on a transmission electron microscope (Philips CM 20 TEM). Particle size distribution of the nanoparticles was determined by manual counting of several hundreds of particles.

Figure 2A:
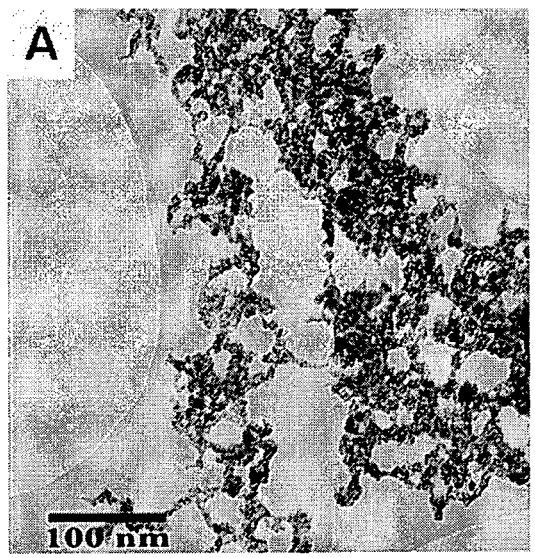
Figure 2B:
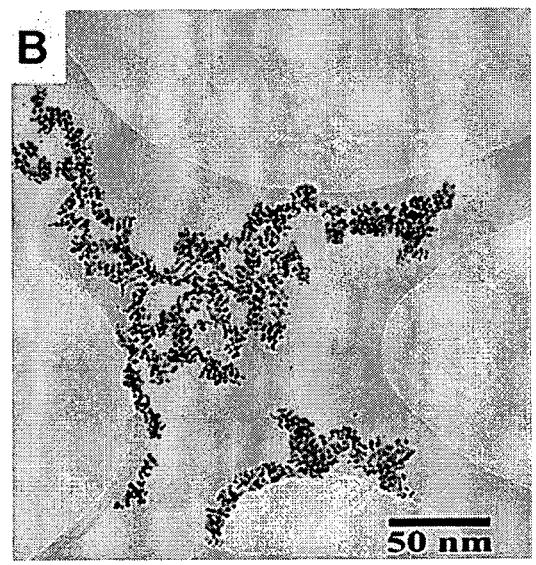
Figure 2C:
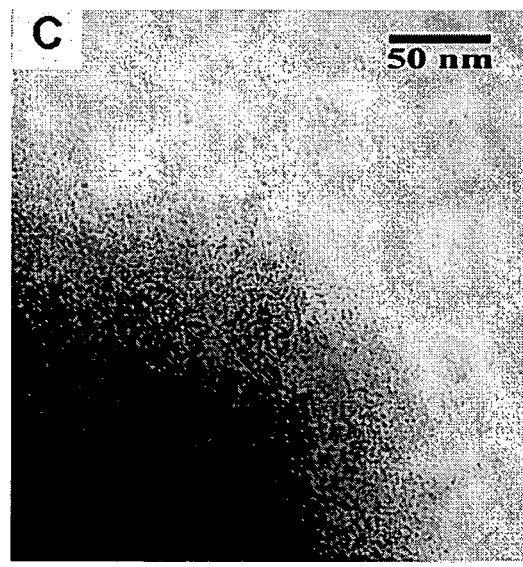
Figure 2D:
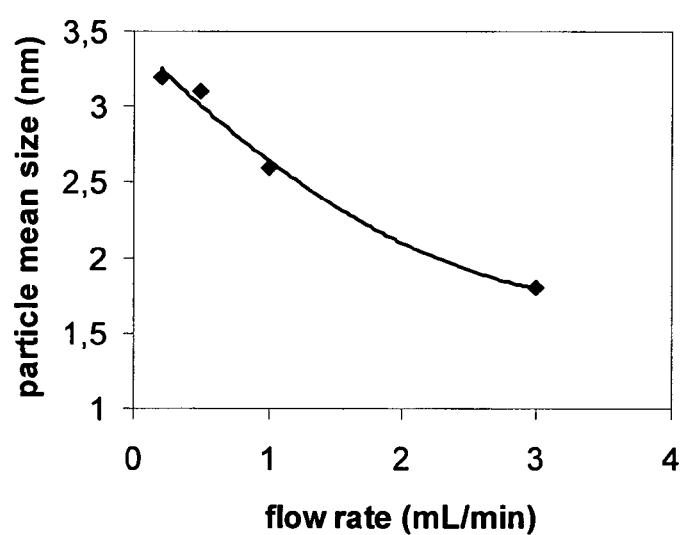

The obtained results are shown in FIGS. 2a-2d. FIGS. 2a-2c show TEM images of Pt nanoparticles synthesized at various flow rates: in image 2a using 0.2 mL/min, in 2b using 1 mL/min and in 2c using 3 mL/min. In FIG. 2d the average particle size can be seen as the function of the applied flow rates.

The narrow particle size distribution of the synthesized nanoparticles and the easy and fine tuneability of the particle size distribution by changing the reaction parameters (in this case the flow rate) is clearly shown by TEM particle size analysis. The size of Pt particles is increased with decreasing flow rate, because the metal ions of the starting solution spend longer time going through the heated reactor zone, which results in a higher probability of aggregation of the newly-formed crystalline seeds resulting bigger nanoparticles. Using higher flow rate, the time period given for the growth of nanoparticles is shorter.

Conclusion: Using the 50 device of invention employing the process according to invention, Pt nanoparticles could be synthesized in well defined particle size, in a short time in gram scale. Stored at room temperature, the obtained colloidal solutions were stable in each case; aggregation of nanoparticles could not be observed. Due to the characteristics of device 50, size-selective optimization could be performed in a short time. Systematic changing of the flow rate during synthesis resulted that the particle size of each samples taken from the product were in the range between 1.5 and 3.5 nm.

EXAMPLE 2

Preparation of Platinum-Iron (Pt—Fe) Bimetallic Nanoparticles

During the experiments both 9 and 10 feeding pumps of 1a and 1b feeding units and also the first 2 reactor unit and the second 3 reactor unit were used. The synthesis of platinum nanoparticles, used as templates in this experiment, was carried out in the first 2 reactor unit, based on the process described above. $6 \times 10^{-3}$ M hexachloroplatinic acid $H_2PtCl_6 \times 6H_2O$ (Aldrich) solution was prepared as a mixture of methanol: water=9:1, then PVP polymer (poly(vinyl-pyrrolidone), Aldrich) was added in a 10-fold monomer excess to $Pt^{4+}$ ions. After setting the reaction parameters (temperature: 150° C., pressure: 45 bar, flow rate: 1 mL/min), the system was flushed with methanol and the experiment was started. The first starting liquid from the starting liquid reservoir 7 was pumped into 2 reactor unit by the 9 feeding pump where particle formation took place. $6 \times 10^{-3}$ M iron-chloride (FeCl$_2$, Aldrich) was pumped by 10 feeding pump with variable flow rates into the T-shaped 5 mixing unit where it was mixed with the colloidal solution containing Pt nanoparticles formed in 2 reactor unit. This combined reaction mixture entered to the 15 reactor zone (also heated to 150° C.), where iron was combined to platinum. The product is a colloidal solution containing Pt—Fe bimetallic nanoparticles which is extremely useful in selective catalytic reactions. The synthesized colloidal solution was collected in the 21 product reservoir. After the synthesis, the product was analyzed by transmission electron microscope with the method described above.

Figure 3:
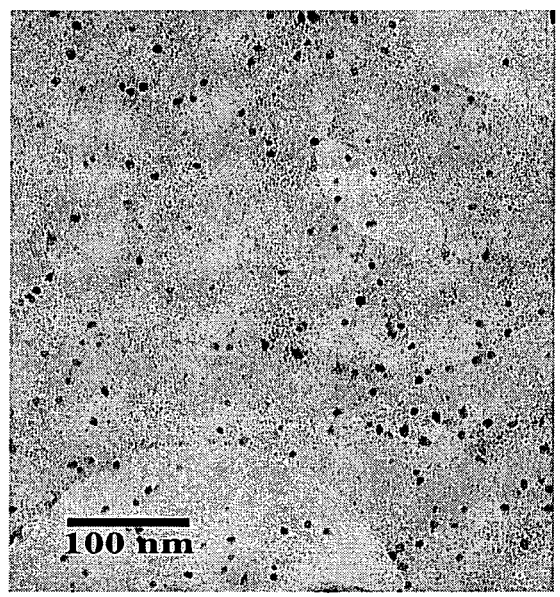

TEM image of Pt—Fe bimetallic nanoparticles can be seen in FIG. 3. The size of particles is considerably different compared to the previous example; it increased to the 10 nm range by incorporating another element, the iron, into the existing Pt blocks.

Conclusion: the 50 device of invention together with the process of invention was proven to be capable of the preparation of bimetallic nanoparticles having outstanding importance in catalysis. With the relative ratio of the flow rates of the starting materials and with its systematic changing, the composition and nanostructure of the product can be varied efficiently and extremely quickly in a wide range.

EXAMPLE 3

Preparation of Semiconductor (Cdse) Nanoparticles

CdSe nanocrystals forming colloidal solution were prepared by high temperature decomposition of the starting materials in continuous flow system using the 50 device of invention. In the first step starting solution was prepared under argon atmosphere: 47.5 mg ($6 \times 10^{-4}$ mol) of selenium powder (Se, Aldrich) was dissolved in 10 mL of trioctylphosphine (TOP, Aldrich). Under continuous stirring, 32 mg ($1.4 \times 10^{-4}$ mol) of cadmium acetate (Cd(AcO)$_2$, Aldrich) and 1.5 g ($3.9 \times 10^{-4}$ mol) of trioctylphosphine oxide (TOPO, Aldrich) were added to the solution. The obtained mixture was stirred for additional 10 minutes at 40° C. Then this starting solution was pumped from 7 starting liquid reservoir into the 2 reactor unit using the 9 feeding pump. The CdSe semiconductor-type ("quantum dot") nanocrystals were prepared in the second 3 reactor unit using previously chosen and set reaction conditions: the reaction temperature was varied between 180 and 300° C., the pressure was set to 100 bar, while the flow rate was varied between 1 and 10 mL/min. The outcome of the reaction was followed by an optionally attachable on-line spectroscopic unit, which was continuously detecting the optical properties of the colloidal solution in the flow-through cell. It follows from the well known properties of the semiconductor "quantum dots" that the wavelength of the absorbed and emitted light is strongly dependent on the size of the particles, accordingly, the 4 unit for collecting and analyzing the product of the reaction equipped with an on-line detector provided continuous information about the synthesized nanoparticles and the parameters describing them. The change in the properties of the reaction products derived from the systematic alteration of the reaction parameters could be followed precisely by the information coming from the on-line detector.

Figure 4A:
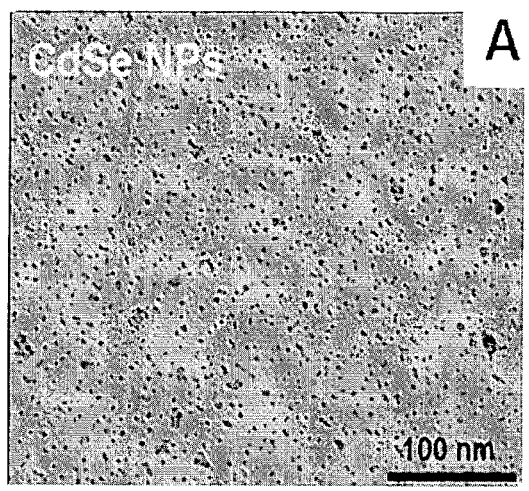
Figure 4B:
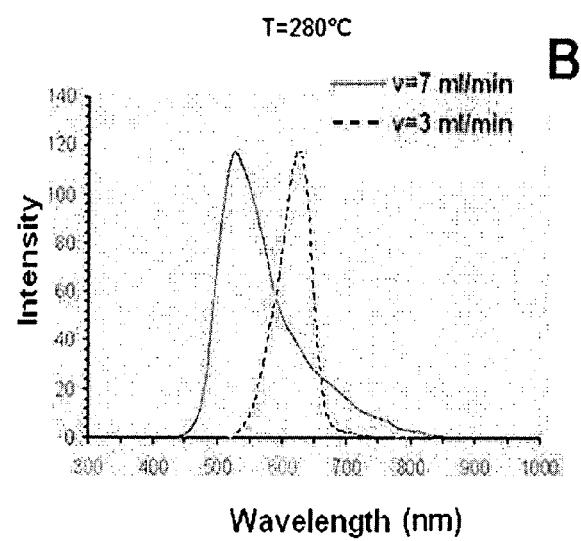

The obtained results are represented in FIGS. 4a and 4b. On FIG. 4a TEM image of CdSe nanocrystals; on FIG. 4b emission spectra of colloidal solutions containing CdSe nanocrystals synthesized at different flow rates can be seen.

The TEM analysis (FIG. 4a) of the synthesized samples clearly shows that CdSe nanocrystals were synthesized selectively, in a well defined, narrow particle size range (2-3 nm) using the 50 device of invention employing the process of invention. In addition, using the 20 on-line detector it is clearly seen, that the size of the obtained nanoparticles were modified easily and quickly by changing the flow rate, which was indicated by the significant shifting of the wavelength of the emitted light.

Conclusion: CdSe-type nanoparticles having well-defined particle size range were successfully synthesized in the 50 device of invention employing the process of invention. The optionally attachable on-line spectroscopic unit was suitable for the continuous on-line detection of the quality of the synthesized product. Using the 20 optical detector we demonstrated that increasing the flow rate, the particle size could be reduced easily and quickly, furthermore, an immediate feedback is obtained from the process using this unit.

EXAMPLE 4

Preparation of 2-(4-isobutylphenyl)propanoic acid nanoparticles

During the experiments 2-(4-isobutylphenyl)propanoic acid nanoparticles were prepared by the 50 device of invention. The starting solution was prepared by dissolving 3 g dextran (Aldrich) in the aqueous solution of 1.35 g 2-(4-isobutylphenyl)propanoic acid sodium salt (Aldrich) in 100 mL distilled water at 25° C. The prepared starting solution was pumped by the 1a feeding unit into the 2 first reactor unit with 3 mL/min flow rate. Meanwhile, using the second 1b feeding unit, a $5 \times 10^{-3}$ M hydrochloric acid solution was pumped into the 5 T-shaped mixing unit with 0.5-1.2 mL/min flow rate, where it was mixed with the solution containing 2-(4-isobutylphenyl)propanoic acid sodium salt coming from the first 2 reactor unit. The nanoparticles were continuously produced at atmospheric pressure due to the precipitating effect of the hydrochloric acid solution pumped into the 5 T-shaped mixing unit. The produced colloidal solution, after passing the 3 second reactor unit, reaches the 4 integrated DLS-analyzer (Dynamic Light Scattering) which can detect the particle size of the obtained nanoparticles continuously. The particle size of the synthesized nanoparticles can be controlled by the flow rates, pressure and the amount of dextran in a wide range. In FIG. 5, particle size and particle size distribution results obtained from light scattering measurements are demonstrated.

The structure of the 2-(4-isobutylphenyl)propanoic acid nanoparticles prepared by the solvent-antisolvent precipitation method was investigated by X-ray diffraction analysis using a Philips PW1050/1870 RTG powder-diffractometer. The measurements showed that the particles are amorphous. The wide reflection between 15 and 20 2Θ values indicates the amorphous structure of the dextran, the reflections characteristic for the crystalline 2-(4-isobutylphenyl)propanoic acid cannot be found. The X-ray diffractograms are demonstrated in FIG. 6.

EXAMPLE 5

Preparation of 1-[4-ethoxy-3-(6,7-dihydro-1-methyl-7-oxo-3-propyl-1H-pyrazolo[4,3-d]pyrimidin-5-yl)phenylsulfonyl]-4-methylpiperazine nanoparticles During the experiments 1-[4-ethoxy-3-(6,7-dihydro-1-methyl-7-oxo-3-propyl-1H-pyrazolo[4,3-d]pyrimidin-5-yl)

phenylsulfonyl]-4-methylpiperazine nanoparticles were prepared with the device according to the present invention. As a starting solution, 250 mg 1-[4-ethoxy-3-(6,7-dihydro-1-methyl-7-oxo-3-propyl-1H-pyrazolo[4,3-d]pyrimidin-5-yl)phenylsulfonyl]-4-methylpiperazine citrate (SD) dissolved in 100 mL distilled water was used. The prepared solution was passed into the 2 reactor unit with 3 mL/min flow rate using the 1a feeding unit. Meanwhile, using the second 1b feeding unit, a solution of 25 mg Carbopol 980 (Lubrisol) dissolved in 100 mL distilled water was passed into the 5 T-shape mixing unit with 1 mL/min flow rate, where it was mixed with the solution containing 1-[4-ethoxy-3-(6,7-dihydro-1-methyl-7-oxo-3-propyl-1H-pyrazolo[4,3-d]pyrimidin-5-yl)phenylsulfonyl]-4-methylpiperazine citrate coming from the first 2 reactor unit. The nanoparticles are continuously produced at atmospheric pressure due to the polyelectrolyte complex formation by Carbopol 980 solution passed into the 5 T-shaped mixing unit. The produced colloidal solution driven through the second 3 reactor unit gets to the 4 dynamic light scattering unit integrated to the device, which can detect the particle size of the obtained nanoparticle continuously. The size of the nanoparticles can be controlled in wide range by changing the flow rates, pressure and the amount of the applied Carbopol 980 (see FIG. 7).

EXAMPLE 6

Preparation of 2-ethoxy-1-({4-[2-(2H-1,2,3,4-tetrazol-5-yl)phenyl]phenyl}methyl)-1H-1,3-benzodiazole-6-carboxylic acid cyclohexyl 1-hydroxyethyl carbonate ester nanoparticles During the experiments 2-ethoxy-1-({4-[2-(2H-1,2,3,4-tetrazol-5-yl)phenyl]phenyl}methyl)-1H-1,3-benzodiazole-6-carboxylic acid cyclohexyl 1-hydroxyethyl carbonate ester nanoparticles were prepared with the device according to the present invention. As a starting solution, 100 mg 2-ethoxy-1-({4-[2-(2H-1,2,3,4-tetrazol-5-yl)phenyl]phenyl}methyl)-1H-1,3-benzodiazole-6-carboxylic acid cyclohexyl 1-hydroxyethyl carbonate ester and 200 mg polyethyleneglycol (PEG 6800, Evonik) were dissolved in 100 mL 2-(2-ethoxy-ethoxy)ethanol. The prepared solution was passed into the 2 reactor unit with 1 mL/min flow rate by the 1a feeding unit. Meanwhile, using the second 1b feeding unit, distilled water was passed into the 5 T-shape mixing unit with 1 mL/min flow rate, where it was mixed with the solution containing 2-ethoxy-1-({4-[2-(2H-1,2,3,4-tetrazol-5-yl)phenyl]phenyl}methyl)-1H-1,3-benzodiazole-6-carboxylic acid cyclohexyl 1-hydroxyethyl carbonate ester coming from the first 2 reactor unit. The nanoparticles are continuously produced at atmospheric pressure due to the precipitating effect of the distilled water passed into the 5 T-shaped mixing unit. The produced colloidal solution driven through the second 3 reactor unit gets to the 4 dynamic light scattering unit integrated to the device, which can detect the particle size of the obtained nanoparticles continuously. The size of the nanoparticles can be controlled in wide ranges by changing the flow rate, pressure and the amount of the applied poly(ethyleneglycol) (see FIG. 8).

EXAMPLE 7

Preparation of (3R,4S)-1-(4-fluorophenyl)-3-[(3S)-3-(4-fluorophenyl)-3-hydroxypropyl]-4-(4-hydroxyphenyl)azetidin-2-one nanoparticles During the experiments, (3R,4S)-1-(4-fluorophenyl)-3-[(3S)-3-(4-fluorophenyl)-3-hydroxypropyl]-4-(4-hydroxyphenyl)azetidin-2-one nanoparticles were prepared with the device according to the present invention. As a starting solution, 200 mg (3R,4S)-1-(4-fluorophenyl)-3-[(3S)-3-(4-fluorophenyl)-3-hydroxypropyl]-4-(4-hydroxyphenyl)azetidin-2-one and 200 mg poly(vinyl-pyrrolidone) (PVP K-25, Aldrich) were dissolved in 100 mL dimethyl sulfoxide. The prepared solution was passed into the 2 reactor unit with 0.3 mL/min flow rate by the 1a feeding unit. Meanwhile, using the second 1b feeding unit, distilled water was passed into the 5 T-shape mixing unit with 1.2 mL/min flow rate, where it was mixed with the solution containing (3R,4S)-1-(4-fluorophenyl)-3-[(3S)-3-(4-fluorophenyl)-3-hydroxypropyl]-4-(4-hydroxyphenyl)azetidin-2-one coming from the first 2 reactor unit.

The nanoparticles are continuously produced at atmospheric pressure due to the precipitating effect of the distilled water passed into the 5 T-shaped mixing unit. The produced colloidal solution driven through the second 3 reactor unit gets to the 4 dynamic light scattering unit integrated to the device, which can detect the particle size of the obtained nanoparticles continuously. The size of the nanoparticles can be controlled in wide range by changing the flow rates, pressure and the amount of the applied polyvinyl-pyrrolidone) (see FIG. 9). We emphasize that due to the cooling of the countercurrent heat-exchanger applied in the device of invention, the process for preparing metallic nanoparticles is excellently reproducible. In Example 8, platinum nanoparticles were prepared. During the experiments, two types of 14, 16 heat-exchangers were used. In the first case a unit based on air-cooling, while in the second case a countercurrent heat-exchanger was integrated to the device. In order to investigate the reproducibility, the experiments were repeated five times using the same experimental parameters. The analysis of the samples was carried out using a transmission electron microscope (Philips CM 20 TEM).

EXAMPLE 8

Preparation of Platinum (Pt) Nanoparticles

In the first step starting solution was prepared by the following way: $6\times10^{-3}$ M hexachloroplatinic acid $H_2PtCl_6 \cdot 6H_2O$ (Aldrich) solution was prepared in a mixed solution of methanol: water=9:1, then PVP polymer (poly(vinyl-pyrrolidone), Aldrich) was added in 10-fold monomer excess to $Pt^{4+}$ ions. The role of the polymer is to prevent the aggregation of Pt nanoparticles, in order to obtain a stable colloidal solution as the result of the synthesis.

In the second step reaction parameters (temperature, pressure, and flow rates) were set by the 22 control unit. The experiment was carried out by using 1 mL/min flow rate, 150° C. reaction temperature (in the first 2 reactor unit's 13 reactor zone) and 45 bar pressure.

Before the reaction, the experimental system was flushed with methanol which was pumped into the 2 reactor unit by the 9 feeding pump. After confirming that the system does not contain any impurities and the 13 reactor zone keeps the set parameters constantly, the starting solution was placed into the 7 starting liquid reservoir and the feeding pump was started. Using the mentioned 1 mL/min flow rate, it took 5 minutes until the first drops of the synthesized colloidal solution appeared in the 21 product reservoir. Analysis of the samples was carried out on a transmission electron microscope (Philips CM 20 TEM). Particle size distribution of the nanoparticles was determined by manual counting of several hundreds of particles.

The obtained results are represented in Fig/Table 10. From the results it can be established that using the countercurrent heat-exchanger, the mean particle size of the Pt nanoparticles was ca. 3.5-4 nm with homogeneous particle size distribution, which value was well-reproduced according to the determination of the repeated experiments. Using the air-cooled unit, however, the size of the produced nanoparticles was between 8 and 15 nm with low reproducibility.

The size of the Pt particles increases if the efficiency of the cooling is lower, i.e. the reaction mixture cools down more slowly. Due to the slower cooling of the reaction mixture, the nanoparticles spend more time in the elevated temperature medium, accordingly, the probability of aggregation of crystalline seeds increases which results in the formation of bigger nanoparticles.

Conclusion: Using 50 device of invention and applying the countercurrent heat-exchanger connected to the device, Pt nanoparticles were synthesized successfully in well defined particle size and with good reproducibility.

The invention claimed is:

1. A continuous flow device (50) for executing a process of preparation of nanostructures, the device (50) comprising:
    a first feeding unit (1a) with a first feed pump (9) connected to a first raw material source (7);
    a second feeding unit (1b) with a second feed pump (10) connected to a second raw material source (8);
    a first reactor unit (2) with a first reactor-zone unit (13) configured to receive material from the first feeding unit to heat to a given first temperature value and to feed into a first cooling unit (14) comprising a first countercurrent heat-exchanger configured to provide an enhanced rate of heat exchange to decrease particle size of nanostructures being prepared by the device;
    a mixing unit (5) configured to receive an output from the first cooling unit (14) and second raw material from the second feeding unit (1b);
    a second reactor unit (3) with a second reactor-zone unit (15) configured to receive output from the mixing unit (5) and to be heated to a given second temperature value to feed into a second cooling unit (16) comprising a second countercurrent heat-exchanger configured to provide an enhanced rate of heat exchange to decrease particle size of nanostructures being prepared by the device;
    at least one pressure controller (18) arranged in a flow path defined by the first reactor unit (2) and the second reactor unit (3) and configured to set a pressure value in the flow path;
    a control unit (22) configured to control at least one of the pressure value set by the pressure controller (18), the given first temperature value, and the given second temperature value;
    wherein the respective cooling units (14, 16) are configured to terminate the process of preparation of nanostructures.

2. The device according to claim 1 further comprising a final product analyzer unit (4) comprising a dynamic light scattering analyzer operatively connected to the first cooling unit (14) and the second cooling unit (16) to continuously monitor and determine particle size and particle size distribution of the nanostructures being prepared and to adjust the first cooling unit (14) and the second cooling unit (16) in response to determined properties of the nanostructures, the analyzer unit (4) being connected to the flow path after the second reactor unit (3).

3. The device according to claim 1, wherein the pressure controller (18) is inserted into the flow path between the second reactor unit (3) and the analyzer unit (4) to maintain a constant pressure value along the flow path.

4. The device according to claim 1, wherein the device (50) is configured to output nanostructures comprising nanoparticles with at least one constituent.

5. The device according to claim 1, wherein the device (50) is configured to output nanostructures comprising nanoparticles with at least one constituent comprises one of a metal or biologically active organic molecules.

6. The device according to claim 1, wherein the device (50) is configured to output nanostructures comprising core-shell type nanoparticles.

7. The device according to claim 1, wherein the device (50) is configured to output nanostructures chosen from the group of consisting of: nanoemulsions and colloidal solution with at least one constituent comprising a metal or biologically active organic molecules.

8. The device according to claim 7, wherein biologically active organic molecules comprise active pharmaceutical ingredients.

9. A method of preparing nanostructures, the method comprising:
    feeding a first raw material from a first raw material source (7) to a first reactor unit (2);
    a first reactor-zone (13) of the first reactor unit (2) heating the first raw material to a given first temperature value;
    feeding an output of the first reactor zone (2) to a first cooling unit (14) comprising a first countercurrent heat-exchanger to provide an enhanced rate of heat exchange to decrease particle size of nanostructures being prepared;
    mixing output from the first cooling unit (14) with second raw material from a second feeding unit (1b) using a mixing unit (5);
    feeding output from the mixing unit (5) to a second reactor unit (3);
    a second reactor-zone (15) of the second reactor unit (3) heating the output from the mixing unit (5) to a given second temperature value;
    feeding an output of the second reactor zone (3) to a second cooling unit (14) comprising a second countercurrent heat-exchanger to provide an enhanced rate of heat exchange to decrease particle size of nanostructures being prepared;
    controlling pressure in the first reactor unit (2) and the second reactor unit (3) to a given pressure value;
    controlling temperature in the first reactor zone (13) and in the second reactor zone (15).

10. The method according to claim 9, further comprising:
    analyzing an output of the second reactor unit (3) with a dynamic light scattering analyzer to continuously monitor and determine particle size and particle size distribution of the output of the second reactor unit (3);
    adjusting the first cooling unit (14) and the second cooling unit (16) in response to determined properties of output of the second reactor unit (3).

11. The method according to claim 9, further comprising outputting from the second cooling unit (14) core-shell type nanoparticles.

12. The method according to claim 9, further comprising outputting from the second cooling unit (14) nanoparticles of biologically active organic molecules.

13. The method according to claim 12, wherein outputting from the second cooling unit (14) nanoparticles of biologically active organic molecules comprises outputting nanoparticles of active pharmaceutical ingredients.

14. The method according to claim 9, further comprising outputting from the second cooling unit (14) nanostructures chosen from the group consisting of: nanoemulsions and colloidal solution with at least one constituent, preferably a metal or biologically active organic molecules.

* * * * *